United States Patent [19]

Tomalia et al.

[11] B 3,996,204

[45] Dec. 7, 1976

[54] NOVEL N-(AR-VINYLBENZYL)AZIRIDINES

[75] Inventors: Donald A. Tomalia; Jerry D. DeVrieze, both of Midland, Mich.

[73] Assignee: The Dow Chemical Company, Midland, Mich.

[22] Filed: Feb. 19, 1974

[21] Appl. No.: 443,563

[44] Published under the second Trial Voluntary Protest Program on February 24, 1976 as document No. B 443,563.

Related U.S. Application Data

[62] Division of Ser. No. 246,872, April 24, 1972, Pat. No. 3,833,557.

[52] U.S. Cl. .............................. 526/263; 526/284; 526/293; 526/296; 526/297; 526/310; 526/320; 526/328; 526/347

[51] Int. Cl.² ............... C08F 26/06; C08F 126/06; C08F 226/06

[58] Field of Search ............... 260/88.1 PA, 88.3 R, 260/82.1, 85.5 B, 85.5 R, 86.1 N, 85.7, 87.5 R, 88.1 R

[56] References Cited

UNITED STATES PATENTS 3,226,372   12/1965   Tousignant et al. ..... 260/88.1 PA X
3,833,557   9/1974   Tomalia et al. ........ 260/88.1 PA X

*Primary Examiner*—William F. Hamrock
*Attorney, Agent, or Firm*—L. W. White; G. R. Plotecher

[57] ABSTRACT

Novel N-(m or p-vinylbenzyl)aziridines are disclosed which correspond to the structural formula

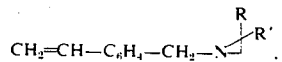

wherein R and R' are hydrogen or lower alkyl. They are highly reactive difunctional monomers which can be homopolymerized or copolymerized to form many useful polymers.

11 Claims, No Drawings

NOVEL N-(AR-VINYLBENZYL)AZIRIDINES

This is a division of application Ser. No. 246,872 filed Apr. 24, 1972, U.S. Pat. No. 3,833,557.

BACKGROUND OF THE INVENTION

N-Benzylaziridine is conventionally prepared by reacting benzyl chloride or bromide with aziridine (ethylenimine). The process is conducted in a polar solvent (e.g. methanol) and in the presence of an acid acceptor and/or an excess of aziridine reactant. See "Ethylenimine and Other Aziridines" by O. C. Dermer and G. E. Ham, Academic Press, Inc., N. Y. (1969) pages 125–6.

SUMMARY OF THE INVENTION

We have discovered a class of novel compounds. They are N-(m or p-vinylbenzyl)aziridines corresponding to the structural formula

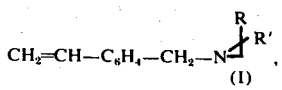

(I)

wherein R and R' are each independently hydrogen or lower alkyl of from 1 to 4 carbon atoms. Preferably, R is hydrogen and R' is hydrogen, methyl or ethyl. Most preferably, R and R' are each hydrogen.

The novel compounds are conveniently prepared in accordance with the aforementioned process by using as reactants m or p-vinylbenzyl chloride or bromide and aziridines corresponding to the structural formula

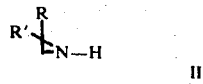

II wherein R and R' have the aforesaid meaning.

Formula II includes aziridine, 2-methylaziridine, 2-ethylaziridine, 2-butylaziridine, 2,2-dimethylaziridine, 2,2-dibutylaziridine, and the like.

The subject compounds, I, are highly reactive difunctional monomers. They can be homopolymerized or interpolymerized with other vinyl monomers by addition polymerization reactions to form novel addition polymers. Such addition polymers are thermally curable. This is a unique and valuable feature which permits the polymers to be cast as films, molded, etc. and subsequently cured by merely heating them to a temperature sufficient to ring-open the pendant aziridinyl groups. The minimum temperature is measured by warming the materials until a temperature exotherm is observed and recording the temperature. The polymers are thus useful in coating articles with a cured, solvent-resistant coating, in preparing strong films for packaging, in preparing molded articles, etc.

Alternatively, the novel polymers can be cured by reaction with a polyfunctional curing agent(s) bearing a plurality of groups which are reactive with the pendant aziridinyl groups on the polymer. Suitable such compounds include epoxy resins, carboxylated resins (e.g. carboxylated polybutadiene, etc.), organic or inorganic polyacids (e.g. phthalic, terephthalic, trimesic, trimellitic and phosphoric acid and the like), anhydrides, mineral acids, Lewis acids, and other such polyfunctional materials.

DETAILED DISCLOSURE

The above addition polymers are prepared via conventional techniques. See, for example, "Polymer Processes" By C. E. Schildknecht, Interscience Publishers, Inc., N. Y. (1956), Vol. X of the "High Polymers" series, which summarizes the many known types of polymerization processes; the disclosure of which is herewith incorporated by reference thereto. The addition polymers vary in length from dimers to aligomers on up to high molecular weight polymers having a molecular weight of several thousand or more. It is well known to those skilled in the art how to obtain addition polymers within a particular molecular weight range; e.g. by choice of reaction temperature, time, concentration and type of initiator, etc.

Vinyl monomers which are polymerizable in such addition polymerization reactions form a known class of compounds. Any monomer from this known group may be interpolymerized with I to form a useful polymer which can be formed into a useful article.

Suitable such vinyl monomers include vinyl aromatic monomers (e.g. styrene, α-methylstyrene, vinyl-toluene, ar-t-butylstyrene, ar-chlorostyrene, ar,ar dichlorostyrene, ar-bromostyrene, vinylnaphthalene, and the like); conjugated diolefins (e.g. butadiene, 2-chloromethylbutadiene, chloroprene, isoprene, 2,3-dimethyl-1,3-butadiene, and the like); alkyl, hydroxyalkyl and amino-alkyl esters of α,β-ethylenically unsaturated carboxylic acids (e.g. the methyl, ethyl, propyl, butyl, hydroxyethyl, 2-hydroxypropyl, 2-hydroxybutyl, 2-aminoethyl and 2-amino-propyl acrylates, methacrylates, maleates, itaconates and fumarates, and the like); α,β-ethylenically unsaturated carboxamides (e.g. acrylamide, N-methylolacrylamide, methacrylamide, and the like); α,β-ethylenically unsaturated nitriles (e.g. acrylonitrile, methacrylonitrile, fumaronitrile, and the like); alkenyl esters of aliphatic and aromatic acids (e.g. vinyl acetate, isopropenyl acetate, allyl propionate, vinyl propionate, vinyl benzoate, isopropenyl benzoate, and the like); and other such vinyl monomers. Preferred vinyl monomers are of course styrene, butadiene, isoprene, lower alkyl (1–4 carbon atoms) acrylates and methacrylates, and acrylonitrile, based on current commercial availability and economics.

The novel addition polymers contain sufficient amounts of I in interpolymerized form to render the interpolymer thermally curable. Typically, the interpolymers contain at least about 2.5 weight percent of I as a practical minimum. The thermally curable addition polymers when heated for 30 minutes at 140°C. are insoluble (but may be swelled) in toluene at a 1% by weight concentration level.

The compounds in formula I are also useful in the preparation of nonaqueous dispersions as taught in two commonly assigned U.S. patent applications entitled "Process for Preparing High Solids Content Polymer Lacquer Dispersions" by W. A. Crozier and D. H. Klein (attorney docket number C-16,004) and "Vinyl Compositions" by D. H. Klein (attorney docket number C-16,008), both submitted herewith.

The following examples further illustrate the invention.

EXAMPLES

Example 1 N-(p-Vinylbenzyl)Aziridine

Anhydrous methanol (200 ml.), anhydrous potassium carbonate (10.0 g.) and ar-vinylbenzyl chloride (approximately 95% para isomer; 0.05 mol.) were charged to a predried reaction vessel equipped with a stirring means and a drying tube. Aziridine (27.0 ml.; 0.5 mol.) was added dropwise to the stirred reaction mixture. Subsequently, the stirred mixture was maintained at room temperature for 24 hours. The work up comprised adding a diatomaceous earth filtering aid to the reaction mixture, filtering out the solids, removing the solvent from the filtrate under reduced pressure and recovering as the pot residue 7.7 g. of crude product as a yellow/orange liquid. The product was purified by distillative techniques under reduced pressure. The product was thus obtained as a water-white liquid boiling at 50°–52°C. at 0.15–0.20 mm. of Hg pressure. Vapor phase chromatography (VPC) of this fraction showed it to contain 85.7% of the desired product. The compound was obtained from the VPC fractionation and its structure confirmed by infrared (IR) analysis, nuclear magnetic resonance (NMR) and elemental analysis.

Example 2 ar-Vinylbenzylaziridine

To a 1-liter, 3-necked flask equipped with a mechanical stirrer, reflux condenser and dropping funnel was charged 86 g. (2.0 mole) of aziridine, 66 g. of 85% powdered KOH (1.0 mole) and 400 ml. of benzene. The mixture was stirred and heated to reflux and 76.25 g. (0.5 mole) of ar-vinylbenzyl chloride containing 0.1% by weight of p,p'-diphenylphenylene diamine inhibitor was added over 15 minutes. The ar-vinylbenzyl chloride was an isomeric mixture consisting of approximately 60–70% meta isomer and 40–30% para isomer. The reaction mixture was then stirred rapidly under reflux for four hours, cooled to room temperature, filtered through a filter cell and the filtrate concentrated at reduced pressure to give 72.4 g. (91.1%) of crude product. This crude product was distilled at reduced pressure to give 63.1 g. (79.4%) of water-white N-ar-vinylbenzylaziridine b.p. 72°–73°/0.6 mm. whose identity was established by IR and NMR. Its purity was found to be greater than 99% by vapor phase chromatography on a G.E. silicone column (10 ft. × 1/4 in.) at 200°C. and 60 ml./min. helium flow rate.

Example 3 N-(p-Vinylbenzyl)-2-Methylethylenimine

The title compound was prepared in a manner analogous to Example 1. The components were ar-vinyl-benzyl chloride (approximately 95% para isomer, 0.249 mol.), potassium carbonate (50.0 g.), anhydrous methanol (1000 ml.) and 2-methylaziridine (70 ml.; 0.974 mol.). Distillation of the crude product (a brown oil) gave 7.6 g. of a water-white liquid boiling at about 85°C. under 0.2–0.3 mm. of Hg pressure. VPC analysis showed this fraction to contain 87.1% of the desired product. The product was obtained from the VPC fractionation and its structure confirmed by IR, NMR and elemental analysis.

Example 4 N-(ar-Vinylbenzyl)-2,2-Dimethylethylenimine

The title compound was prepared in a manner analogous to Example 2. The reactants were ar-vinyl-benzyl chloride (same meta and para ratio as in Example 2, 0.25 mole), 2,2-dimethylethylenimine (1.0 mole), powdered 85% KOH (0.5 mole) and 200 ml. benzene. The distilled product was obtained in 84.4% yield (based on theory) as a water-white liquid boiling at 82°–84°C. at 0.7 mm. of Hg.

Example 5 N-(ar-Vinylbenzyl)-2-Ethylethylenimine

The title compound was prepared in a manner analogous to Example 4 except 2-ethylethylenimine was used in place of 2,2-dimethylethylenimine. The distilled product was obtained in 77.4% yield (based on theory) as a water-white liquid boiling at 75°–77°C. at 0.4 mm. of Hg.

Example 6 Copolymer of N-(p-Vinylbenzyl)Aziridine and Styrene

A solution of styrene (22.3 g.; 0.214 mol.) and N-(p-vinylbenzyl)aziridine from Example 1 (3.4 g.; 85.7% pure; 0.018 mol.) was charged to a nitrogen purged polymerization vessel along with azobisisobutyronitrile (25 mg.). The vessel was purged with nitrogen for an additional hour, sealed and heated for 33 hours at 61°C. The polymer thus obtained was purified by precipitating it from a toluene solution with methanol. The precipitated polymer was ground in a high shear blender in the presence of 200 ml. of methanol. The ground polymer was collected by filtration, washed with methanol and dried in a vacuum oven at 40°C. The polymer (14.8 g.) thus obtained was a white hard solid having a 1.04% nitrogen content. This corresponds to a copolymer having 11 sytrene units per N-(p-vinylbenzyl)aziridine unit.

A film was cast from a toluene solution of the above copolymer and cured for 1 hour at 60°C. The cured film was insoluble in toluene and had a good tensile strength.

Various curing agents were added to aliquots of a toluene solution of the copolymer and cast as films on glass plates. The results were: (1) Small amounts of glacial acetic acid, levulinic acid, oxalic acid and isophthalic acid and 1,9-nonanedithiol gave films which were partially soluble and/or swelled by toluene. (2) Small amounts of oxalyl chloride and BF$_3$.etherate caused the copolymer to swell and gel immediately while maleic anhydride caused the copolymer to gel slowly as the anhydride dissolved in the medium. (3) An epoxy resin derived from Bisphenol A and epichlorohydrin gave a film which was insoluble in toluene and had good tensile strength. (4) Phenylacetic acid likewise gave a toluene-insoluble film.

All of the films were clear and colorless. Films cast from a toluene solution of the copolymer without any curing agent were readily redissolved in toluene.

Example 7 Homopolymer of N-(p-Vinylbenzyl)Aziridine

A 1 ml. sample of the product of Example 1 containing 2 mg. of azobisisobutyronitrile was polymerized by heating it at 61°C. for approximately 18 hours and subsequently at 70°C. for 9 hours. The polymer thus produced swelled, but did not dissolve, in toluene even after 1 week.

Other monomers as described by I above are similarly prepared by using the appropriate aziridinyl reagent.

Other addition interpolymers are similarly prepared by using the appropriate comonomer, e.g. methyl methacrylate, t-butylstyrene, etc.

The addition polymers may be cast as films having desirable properties, such as tensile strength, or molded into useful articles. Where desirable, the polymers can be cross-linked by heating or treatment with a suitable curing agent, e.g. epoxy resins, to form insoluble, hard cross-linked polymers having many uses, e.g. as containers, ice scrapers, etc.

Alternatively, the addition polymers may be used as cross-linking agents for epoxy resins, carboxylated polymers (e.g. carboxylated polybutadiene), or other polymers bearing a plurality of carboxylic, sulfonic or anhydride groups.

We claim:

1. A thermally curable vinyl addition polymer containing an N-(m or p-vinylbenzyl)aziridine corresponding to the structural formula

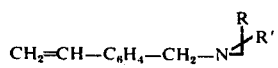

wherein R and R' are hydrogen or alkyl of from 1 to 4 carbon atoms in interpolymerized form in sufficient quantity to make the polymer thermally curable.

2. The polymer defined by claim 1 having at least 2.5 weight percent of N-(m or p-vinylbenzyl)aziridine.

3. The polymer defined by claim 1 wherein said polymer is an interpolymer of said N-(m or p-vinyl-benzyl)-azridine and a vinyl aromatic monomer.

4. The polymer defined by claim 3 wherein said vinyl aromatic monomer is styrene, α-methylstyrene vinyltoluene, ar-t-butylstyrene, ar-chlorostyrene, ar, ar-dichlorostyrene, ar-bromostyrene, or vinylnaphthalene.

5. The polymer defined by claim 4 wherein said vinyl monomer is styrene.

6. The polymer defined by claim 1 wherein said polymer is an interpolymer of said N-(m or p-vinyl-benzyl) aziridine and a conjugated diolefin.

7. The polymer defined by claim 1 wherein said polymer is an interpolymer of N-(m or p-vinylbenzyl) aziridine and an alkyl, hydroxyalkyl or amino alkylester of an α β-ethylenically unsaturated carboxylic acid.

8. The polymer defined by claim 1 wherein said polymer is an interpolymer of N-(m or p-vinylbenzyl) aziridine and an α β-enthylenically unsaturated carboxamide.

9. The polymer defined by claim 1 wherein said polymer is an interpolymer of N-(m or p-vinylbenzyl) aziridine and an α β-ethylenically unsaturated nitrile.

10. The polymer defined by claim 1 wherein said polymer is an interpolymer of N-(m or p-vinylbenzyl) aziridine and an alkenyl ester of an alphatic or aromatic acid.

11. The polymer defined by claim 1 wherein said polymer is a homopolymer of said N-(m or p-vinylbenzyl) aziridine.